United States Patent [19]
Ripoche et al.

[11] Patent Number: 6,052,609
[45] Date of Patent: Apr. 18, 2000

[54] ELECTROPHYSIOLOGICAL DEVICE

[75] Inventors: André Ripoche, Vitry sur Seine; Pierre-Marie Baudonniere, Paris, both of France

[73] Assignee: Centre National De La Recherche Scientifique, Paris, France

[21] Appl. No.: 09/011,719

[22] PCT Filed: Sep. 4, 1996

[86] PCT No.: PCT/FR96/01351

§ 371 Date: Feb. 13, 1998

§ 102(e) Date: Feb. 13, 1998

[87] PCT Pub. No.: WO97/08988

PCT Pub. Date: Mar. 13, 1997

[30] Foreign Application Priority Data

Sep. 8, 1995 [FR] France .................................. 95 10565

[51] Int. Cl.[7] .................................................. A61B 5/0408
[52] U.S. Cl. ........................ 600/383; 600/383; 600/386; 600/509; 600/544; 600/546
[58] Field of Search .................... 600/372, 382, 600/383, 386, 388, 393, 509, 544–547

[56] References Cited

U.S. PATENT DOCUMENTS 3,880,146 4/1975 Everett et al. .

4,817,627 4/1989 Cohen et al. .

FOREIGN PATENT DOCUMENTS 0 165 141 12/1985 European Pat. Off. .

OTHER PUBLICATIONS

H. Iguchi, et al., "Wearable Electroencephalograph System with Preamplified Electrodes"; *Medical & Biological Engineering & Computing*, Jul. 1994, pp. 459–162.

"Signale vom Herzen"; *Funkschau*, 1985, pp. 76–78.

*Primary Examiner*—Linda C. M. Dvorak
*Assistant Examiner*—Bryan K. Yarnell
*Attorney, Agent, or Firm*—Staas & Halsey LLP

[57] ABSTRACT

An electrophysiological sensing device, such as a helmet, that can be fitted to a living subject. The device includes a set of electrodes for detecting electromagnetic signals and inputting the signals to a processor. The set of electrodes includes working electrodes having at least one acquisition electrode in a selected position on the subject, and an additional electrode to be connected to the processor as a floating ground. An output of each working electrode is equipped with a first impedance adapter. A common electrical supply is provided for these first impedance adapters. A circuit capable of maintaining an intermediate electrical potential, dependant from the electrical supply, is provided at the electrical potential of the additional electrode.

37 Claims, 2 Drawing Sheets

ELECTROPHYSIOLOGICAL DEVICE

BACKGROUND OF THE INVENTION

1. Field of the Invention

The invention concerns the field of electrophysiology, and especially the detection by electrodes, in a difficult medium and in order to record them, of electrophysiological signals of the electromagnetic type, emitted by a subject.

2. Description of the Related Art

It concerns more particularly the devices of the type comprising sensor equipment that can be fitted to a subject, and provided with a set of electrodes for detecting electromagnetic signals, in order to deliver them in the form of output signals to inputs of processing means capable, moreover, of processing them prior to storage.

Such a set generally comprises working electrodes having at least one acquisition electrode installed in a selected position in or on the sensor equipment, and also an additional electrode to be connected to the processing means as a floating ground.

By sensor equipment there is to be understood, for example, a helmet provided with electrodes intended to detect cerebral activity, of the electroencephalogram type (EEG), or an apparatus intended to detect muscular activity, of the electromyogram type (EMG), or an apparatus intended to detect cardiac activity, of the electrocardiogram type (ECG), or more generally any apparatus for the acquisition of electrophysiological signals.

Furthermore, by subject there is intended to be understood any living being (human or animal), whether clinically ill, and in this case it is a patient, or clinically healthy.

The Applicant observed that, in certain conditions of use, the signals detected by the electrodes of such sensor equipment exhibited a signal/noise ratio (S/N) which was of the order of unity, and consequently did not really represent the activity under examination.

This is particularly the case with examinations intended to detect electrical signals, on the one hand, of very small amplitude, typically of the order of a few microvolts, on subjects that are subjected to imposed displacements, such as, for example, during stimulation of their vestibular system (in order to gather vestibular evoked potentials), and/or, on the other hand, on subjects which are not easy to keep immobile, such as, for example, babies, hyperkinetic subjects or patients suffering from Parkinson's disease.

This is also the case when making recordings in environments which are noisy from an electromagnetic point of view, even when the subject is immobile.

The Applicant observed that the principal cause of this effect of noise interference on the signals could be attributed to the coupled effect of the impedance of the electrodes (typically a few kilo-ohms) and of the electrical loops which are formed by the connecting cables between the electrodes and the processing means. These loops, when they are subjected to displacement in a continuous electromagnetic field, have at their terminals an induced interference voltage comparable to electrical noise.

Such a voltage is so much the more disturbing when, in the case of imposed displacements, it is in phase with the signals representing the activity under examination, and the larger the size of the loop and the greater the impedance of the loop, and consequently of the electrodes, the greater the amplitude of the voltage is.

SUMMARY OF THE INVENTION

The object of the present invention is to improve the situation by providing a solution to this problem of noise interference with the measurements which prevent their analysis.

To this end, the invention proposes a device of the type defined previously, and wherein, on the one hand, the output of each working electrode is equipped with a first impedance adapter means, and on the other hand, a common electrical supply is provided for the first impedance adapter means, and also a circuit, for maintaining an intermediate electrical potential, dependant from this supply, at the electrical potential of the additional electrode, which of course depends on the location at which the said additional electrode is placed. This intermediate potential therefore lies between the respective values of the potentials of the two end terminals of the supply.

Thus, by equipping the output of each working electrode with an impedance adapter means, their output impedance is very markedly reduced, and this tends to eliminate the effect induced by the displacements of the subject. Moreover, since the circuit is connected to an intermediate point of the supply, this makes it possible to define a floating ground which will serve as a reference ground for the device and for the processing means.

According to another characteristic of the invention, the output of the additional electrode is also equipped with a second impedance adapter means.

In a particularly advantageous manner, the first and second impedance adapter means are produced by means of an operational amplifier which, owing to its very small size, can easily be installed at the output of each electrode, or incorporated directly in the electrode, without this involving any noticeable increase in the weight of the sensor equipment.

According to yet another characteristic of the invention, the output of each operational amplifier is coupled to the inverting input thereof.

Thus, by setting up a counter-reaction, the voltage gain of each operational amplifier becomes substantially equal to unity for the signals applied at its non-inverting input. Each operational amplifier is thus transformed into a voltage follower of almost zero output impedance.

Preferably, the respective gains of the first impedance adapter means are substantially equal, which makes it possible to avoid re-normalization of the signals.

In a first embodiment of the device, the output of each electrode is connected to the non-inverting input of the corresponding operational amplifier, which operational amplifier has an output connected to the corresponding input of the processing means. The potential of the output of the additional electrode is the potential of the additional electrode, and consequently, according to the invention, it is equal to the intermediate potential.

In a second embodiment of the device, the output of each working electrode is connected to the non-inverting input of the corresponding operational amplifier, which has an output connected to the corresponding input of the processing means, while the output of the additional electrode is connected to the output of the corresponding operational amplifier, which operational amplifier has a non-inverting input connected to the corresponding input of the processing means and maintained at the intermediate electrical potential, dependant from the supply, by way of the circuit of the additional electrode.

The circuit of the additional electrode preferably comprises first and second resistors, having identical characteristics, respectively between the first and second end terminals of the supply and the non-inverting input of the operational amplifier corresponding to the additional electrode.

But the circuit of the additional electrode may be produced differently, the non-inverting input of the operational amplifier being connected directly to the middle point of the supply.

In each of these two embodiments, it is possible to maintain the additional electrode at an intermediate electrical potential dependant from an intermediate point of the supply, which is in fact the middle point, of a potential substantially equal to zero volts. Consequently, the floating ground which fixes the reference potential of the processing means is also substantially at the potential of zero volts.

The operational amplifier with which the additional electrode is equipped is preferably of the bipolar type or of the field effect type. The same applies to each operational amplifier with which a working electrode is equipped.

It may of course be envisaged that the operational amplifier of the additional electrode is of a given type, while the operational amplifiers of the working electrodes are all of the other type.

When the operational amplifiers of the working electrodes are of the field effect type, it is preferable for the device according to the invention to comprise, between each end terminal of the supply and the non-inverting input of each operational amplifier corresponding to each working electrode, respectively, a first and a second diode which are reverse biased and which have identical characteristics.

This thus limits very markedly the possibilities of electrical breakdown of an operational amplifier, which would make it inoperative and consequently would prevent analysis of the signals detected by the corresponding electrode.

Preferably, the working electrodes also include at least one reference electrode intended to provide one or more reference potentials which will be of service during the processing of the electrical signals issuing from the acquisition electrodes.

Since these reference electrodes are working electrodes, they are of course equipped with the same type of impedance adapter as the acquisition electrodes.

But it is clear that such reference electrodes may be dispensed with if, on the one hand, the number of electrodes is sufficient and if, on the other hand, the acquisition means are capable of calculating a notional reference potential from the whole of the potentials delivered by the acquisition electrodes. This notional potential would then replace the reference potential or potentials delivered normally by the reference electrode or electrodes.

Consequently, as a variant, a device could be provided without reference electrodes but equipped with at least three acquisition electrodes, and the processing means of which are capable of calculating a notional reference potential from the signals delivered by each acquisition electrode.

This notional reference potential represents the mean of the potentials delivered by each acquisition electrode.

According to yet another characteristic of the invention, the supply consists of a battery, or of a plurality of batteries arranged in series, or of rechargeable accumulators, in which the potential difference between the two end terminals is substantially equal to 9 volts.

This method of supply makes it possible on the one hand to secure the fitting onto the subject, and on the other hand to avoid the electrical interference customarily generated by a DC—DC converter, although its use is entirely feasible.

In an application to an EEG, the sensor equipment of the device proposed is an electrophysiological helmet that can be fitted on the head of the subject. The signals detected by the acquisition electrodes are then cerebral activity waves coming from identifiable areas of the brain.

It is thus possible, for example, to detect the evoked potentials of subjects that are subjected to vestibular stimulation, or to study the cerebral activity of subjects that are difficult to immobilise.

Other characteristics and advantages of the invention will be revealed by an examination of the detailed description which follows, and of the accompanying drawings, in which:

The accompanying drawings are substantially of a fixed nature. Consequently, they form an integral part of the description and may not only serve to complete the latter but also contribute to the definition of the invention if need be.

Description of the Preferred Embodiments

Figure 1:
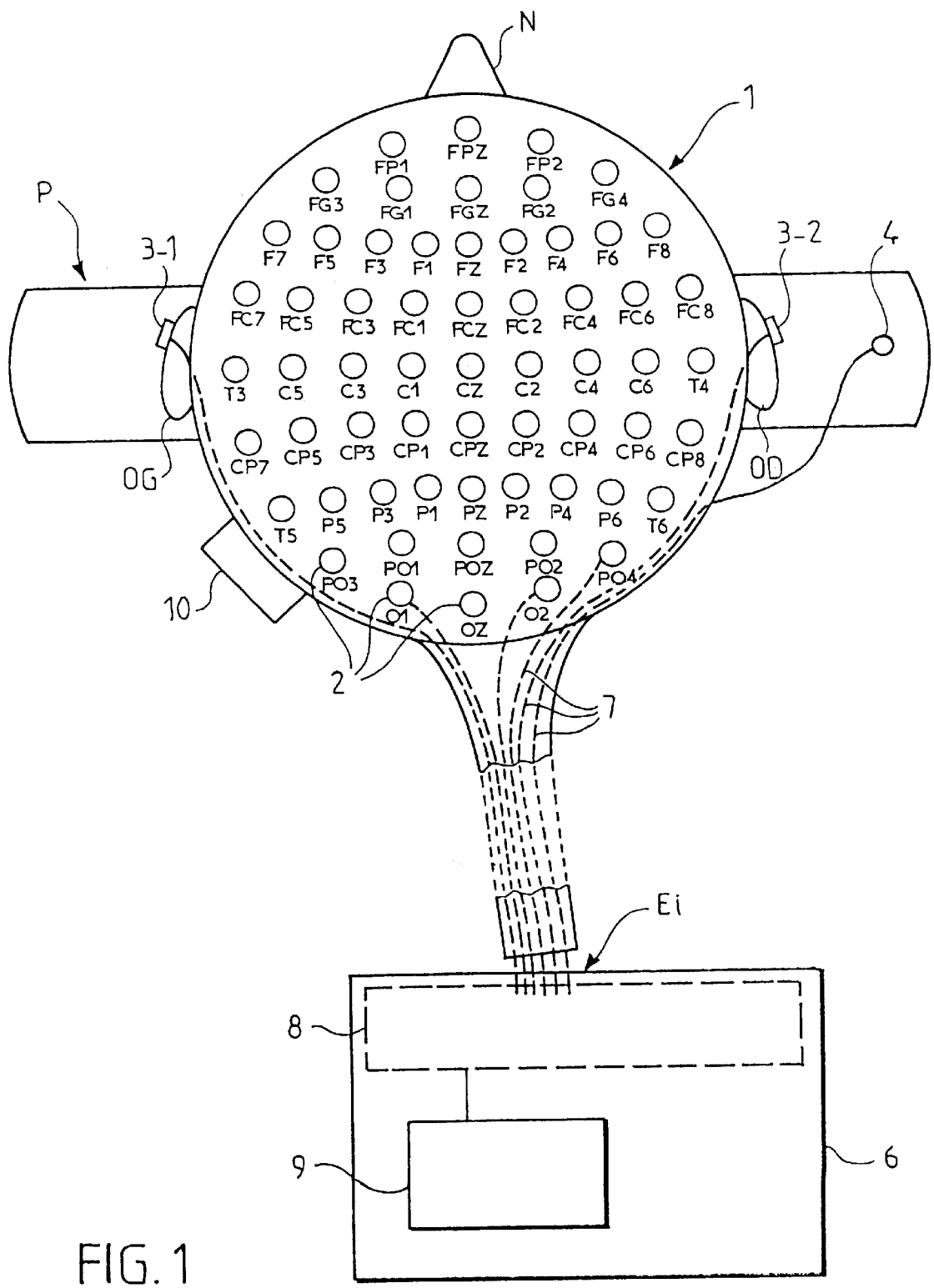
FIG. 1 is a diagram illustrating the principal elements of the device according to the invention in an embodiment intended for an EEG.

Reference is made firstly to FIG. 1 in order to describe an electrophysiological device according to the invention.

In all of the description which follows, it will be considered that the sensor equipment is an electrophysiological helmet 1 intended to detect electrical signals representing evoked potentials of a subject P, especially of a person, subjected to vestibular stimulation. But it is clear that the invention proposed applies to many other fields.

The electrophysiological helmet 1 is produced from a flexible material and its shape is substantially spherical, which makes it possible to fit it on the head of a human subject P, installed, for this type of stimulation, in an armchair (not shown).

Nonetheless, any other helmet or fitting equipped with electrodes for detecting cerebral activity waves on the scalp of a subject may be used, and particularly adhesively secured electrodes.

The helmet 1 comprises a set of electrodes including working electrodes 2 and 3, and also an additional electrode 4.

The working electrodes comprise, on the one hand, acquisition electrodes 2-j (j=1 to n) intended to detect the electrical signals representing evoked potentials emitted by certain areas of the brain in response to stimulation and, on the other hand, one or two, or even three, reference electrodes 3-k (k=1 to 3).

A description will be given here of an acquisition comprising a reference electrode installed on the nose N of the patient, or two reference electrodes placed respectively on the right ear OD and left ear OG to calculate the mean of their respective potentials, or to use the latter separately. But it is also possible to use any other part of the body of the patient as reference potential.

The electrodes 3-k are intended to supply a reference potential representing at each moment the surface potential in proximity to the electrodes, so that it is possible to deduce the true signals of vestibular origin, by subtraction between the electrical signals detected by the acquisition electrodes 2-j and the electrical signals detected by the reference electrodes 3-k.

Each acquisition electrode 2 is installed in the structure of the helmet 1 at a selected location, where it defines a cerebral zone on the scalp of the subject, each cerebral zone being associated with at least one identifiable area of the brain, assumed to be a vestibular projection.

According to the accuracy of the examination, the helmet may have from one to n electrodes, the number n not being limiting.

FIG. 1 shows the respective positions of 61 electrodes with reference to the right ear OD and left ear OG, and also to the nose N of a human subject.

The additional electrode 4 is generally installed on the cheek or the shoulder of the subject P. It makes it possible to fix the value of the potential of the floating ground of the device. The latter will be referred to subsequently.

The output 5 of each electrode 2 to 4 is connected to an input Ei (i=2 to 4) of the processing means 6 by way of an electrical cable 7 having a length of approximately 1 to 1.5 meters.

The processing means 6 comprise processing means 8 intended at least to amplify each signal received, independently, and also memory means 9 intended to store the signals thus amplified for the purpose of their subsequent analysis.

Processing may of course also include one or more filtering operations, and also digitalization prior to storage.

Moreover, the processing means may be arranged in such a way that they can display in real time at least some of the signals representing evoked potentials emitted in response to stimulation, after subtraction of the reference potentials detected by the electrodes 3-k.

Processing may also comprise a step, before display, in which the evoked potentials are examined in relation to the law of motion selected for stimulating the vestibular system of the subject.

Similarly, in order to determine as accurately as possible the areas of the brain involved in the vestibular response to stimulation, an analysis may be made of the evoked potentials by the linear combination of certain acquisition electrodes 2-j of the helmet 1.

Finally, the helmet, like any other recording device, may also comprise electrodes (not shown in the figures) intended to be fixed in the vicinity of the eyelids of the subject in order to register the vertical and horizontal movements of the eyes. Such electrodes are of course connected to the processing means 6.

Figure 2:
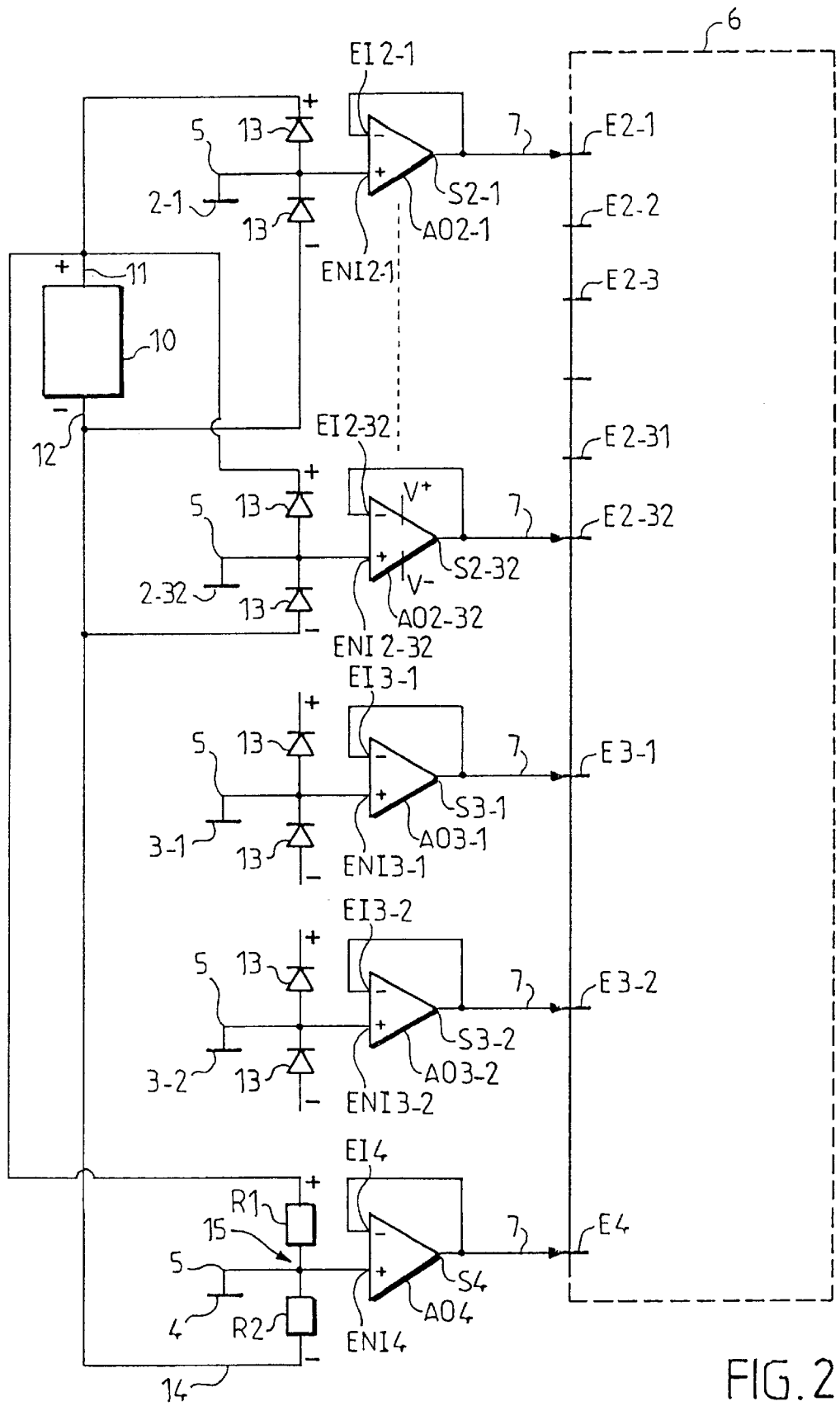
FIG. 2 is a diagram illustrating the impedance adapter means at the output of the electrodes of the sensor equipment according to the invention, in a preferred embodiment.

Reference is now made to FIG. 2, in order to describe in more detail the output 5 of the electrodes 2 to 4 of the helmet 1.

The signals detected by the acquisition electrodes 2-j (j=1 to 32) are delivered to the processing means in the form of a potential difference, the amplitude of which depends on the one hand on the number of neurons involved in the response, and on the other hand on the depth at which the part of the brain which is emitting is located. These potential differences are therefore, generally, of very low intensity, typically a few microvolts.

The electrodes 2 to 4 used by a person skilled in the art have a high output impedance, typically a few kilo-ohms. In fact, their impedance is due to contact with the scalp of the subject, which is effected by means of a conductive paste or a conductive gel.

As explained in the introduction, the displacement of the connecting cables 7 in a continuous electromagnetic field induces an interference potential difference in these cables, and the greater the output impedance of the electrode, the greater this potential difference is.

To eliminate these interference voltages in phase with the stimulation, there are two solutions. The first solution consists in shortening the length of the connecting cables 7 as much as possible. The second solution consists in reducing the output impedance of the electrodes as much as possible.

It is clear that the first solution is not feasible, since it would make it necessary to install a part of the processing means, and especially the amplification part 8, on the helmet 1, which would very markedly increase the weight of the said helmet and could even disturb the measurements.

Consequently, the Applicant had the particularly advantageous idea of installing at the output of each electrode 2 to 4 an impedance adapter means Aoi (i=2 to 4) intended to reduce their output impedance to a value of the order of one ohm. These impedance adapter means have not been shown in FIG. 1 for reasons of space.

Each impedance adapter means AOi consists of an operational amplifier of the field effect type, like that proposed by the company Analog Devices under reference number AD795, or of the bipolar type, like that proposed by the company Linear Technology under reference number LT1012.

Each operational amplifier is mounted as a voltage follower (or in a closed loop), so that its gain is substantially equal to 1, and consequently its output impedance is of the order of one ohm. In order to do this, its output Si (i=2 to 4) is connected directly to its "inverting" input EIi.

An embodiment is preferred in which the output 5 of each of the electrodes 2 to 4 is connected to the non-inverting input ENIi (i=2 to 4) of the corresponding operational amplifier AOi, which has an output Si connected to the corresponding input Ei of the processing means 6.

In this embodiment, the gain of each operational amplifier AOi is equal to +1.

In order to avoid any fresh interference which could arise by reason of the connection between the electrode and the operational amplifier it is preferable for the said operational amplifier to be connected directly to the electrode, or even better, for it to be incorporated directly in the electrode during its manufacture, or even in the structure of the helmet.

Each of these operational amplifiers AOi (i=2 to 4) requires a continuous power supply in order to operate. Consequently, a supply 10 is provided which is installed, for example, on the helmet 1. This supply may of course be installed at any other location not too far from the head of the patient. The supply inputs V+ and V− of an operational amplifier are shown only at A02-32 for reasons of space, but it is clear that each operational amplifier is supplied in the same way. Preferably, the supply is provided from one or more batteries arranged in series, or by means of rechargeable accumulators. The potential difference at the terminals of the supply is preferably equal to 9 volts, the first end point 11 being at a higher potential of +4.5 volts, while the second end point 12 is at a lower potential of −4.5 volts.

This solution is preferred to that which consists in using a DC—DC voltage converter, which sometimes generates interference. Moreover, a battery supply provides improved insulation relative to the surrounding circuits and is safer for the patient, connected to this supply by way of the electrodes, as will be seen hereinafter.

When the operational amplifiers A02-j and A03-k are of the field effect type it is preferable, in order to avoid electrical breakdowns, for their non-inverting input ENIi (i=2 or 3) to be protected. In order to do this, on the one hand, by way of a reverse biased first diode 13, the first end point 11 of the supply 10 is connected to the non-inverting input ENI2-j and ENI3-k of each operational amplifier corresponding to each working electrode 2-j and 3-k, and on the other hand, by way of a second reverse biased diode 13, the second end point 12 of the said supply 10 is connected to the non-inverting input ENI2-j and ENI3-k of each operational amplifier corresponding to each working electrode 2-j and 3-k. These first and second diodes should have substantially identical characteristics.

Preferably, these are diodes with a very small reverse current, typically of a few picoamperes, such as, for example, diodes of the PAD5 type (Pico Ampere Diode with maximum reverse current of 5 pA).

This particularly advantageous assembly makes it possible to block the electrical charges so that the non-inverting input of each operational amplifier thus equipped is not subjected to voltages greater than the respective voltages of the end points 11 and 12 of the supply (±4.5 volts).

On the other hand, whichever type of operational amplifier AO4 is connected to the additional electrode 4, it is essential to provide a circuit 14 making it possible to connect its non-inverting input ENI4 to the supply 10. In fact, this electrode 4 is connected to the processing means 6 and to the patient, so as to define a floating ground for the whole of the device. Preferably, this floating ground is an electrical potential of approximately zero volts.

A first solution consists in connecting the non-inverting input ENI4 of AO4 directly to an intermediate point or middle point of the supply 10. In this way, if the middle point effectively corresponds to the zero volt potential then the non-inverting input ENI4 is at the zero volt potential, just like the ground of the processing means 6, since the latter is connected to the output of AO4 which functions as a voltage follower having a gain of +1.

A second solution consists on the one hand in connecting, by way of a first resistor R1, the first end point 11 of the supply 10 to the non-inverting input ENI4 of the operational amplifier AO4, and on the other hand in connecting, by way of a second resistor R2, the second end point 12 of the said supply 10 to the non-inverting input ENI4 of the operational amplifier AO4. These first and second resistors should have substantially identical characteristics in order to avoid an electrical imbalance.

Thus, an intermediate point 15 is created having a potential substantially equal to zero (except for fluctuations of the characteristics of the resistors), which, by means of AO4, will define the reference floating ground of the device, as indicated above.

This second solution is preferred, since it makes it possible to avoid using an additional unprotected connecting cable between the additional electrode and the middle point of the supply, which would moreover necessitate, in order to be provided, adaptation of the supply.

Another embodiment may be envisaged for the impedance adaptation of the additional electrode 4, in which embodiment the output 5 of the additional electrode 4 is connected to the output S4 of AO4, which has a non-inverting input ENI4 connected to the corresponding input E4 of the processing means 6, and also to the middle point of the supply or to an intermediate potential defined as before by two resistors having identical characteristics, installed respectively between the ends 11 and 12 of the supply.

In the above description, a device fitted on the head of a human subject has been described, but it is clear that such a test device may be adapted for the examination of any living being. This implies that other types of electrophysiological helmet may be used, without thereby departing from the scope of the invention.

Similarly, the invention is not limited to electrophysiological helmets, but concerns any type of sensor equipment provided with electrodes, such as, for example, apparatuses serving for muscular analysis (EMG) or cardiac analysis (ECG).

We claim:

1. Electrophysiological device, comprising:
   sensor equipment that can be fitted to a subject, and provided with a set of electrodes for detecting electromagnetic signals, in order to deliver the electromagnetic signals in the form of output signals to inputs of a processor capable of processing the output signals prior to storage, the set including working electrodes having at least one acquisition electrode in a selected position on the subject, and an additional electrode to be connected to the processor as a floating ground,
   wherein an output of each working electrode is equipped with a first impedance adapter;
   a common electrical supply for the first impedance adapters; and
   a circuit, capable of maintaining an intermediate electrical potential, dependant from this supply, at an electrical potential of the additional electrode.

2. Device according to claim 1, wherein an output of the additional electrode is equipped with a second impedance adapter, also fed by the supply.

3. Device according to claim 2, wherein each of the first and second impedance adapters is an operational amplifier including inverting inputs, non-inverting inputs, and an output.

4. Device according to claim 3, wherein the output of each operational amplifier is coupled to the inverting input thereof.

5. Device according to claim 3, wherein each working electrode has an output connected to the non-inverting input of the corresponding first impedance adapter operational amplifier, which has an output connected to one of the inputs of the processor.

6. Device according to claim 3, wherein the additional electrode has an output connected to the non-inverting input of the corresponding second impedance adapter operational amplifier, which has an output connected to one of the inputs of the processor.

7. Device according to claim 3, wherein the additional electrode has an output connected to the output of the corresponding second impedance adapter operational amplifier, which has a non-inverting input connected to one of the inputs of the processor, and is maintained at the intermediate electrical potential dependant from the supply by way of the circuit of the additional electrode.

8. Device according to claim 3, wherein the circuit of the additional electrode comprises a first resistor between a first end terminal of the supply and the non-inverting input of the second impedance adapter operational amplifier, and a second resistor, equal in value to the first resistor, between a second end terminal of the supply and the non-inverting input of the second impedance adapter operational amplifier.

9. Device according to claim 3, wherein the non-inverting input of the operational amplifier is connected directly to a middle point of the supply.

10. Device according to claim 3, wherein the operational amplifier with which the additional electrode is equipped is a bipolar type.

11. Device according to claim 3, wherein the operational amplifier with which the additional electrode is equipped is a field effect type.

12. Device according to claim 3, wherein each operational amplifier, with which a working electrode is equipped, is a bipolar type.

13. Device according to claim 3, wherein each operational amplifier, with which a working electrode is equipped, is a field effect type.

14. Device according to claim 13, further comprising, between the first end terminal of the supply and the non-inverting input of each operational amplifier corresponding to each working electrode, a first, reverse biased diode and, between the second end terminal of said supply and the non-inverting input of each operational amplifier corresponding to each working electrode, a second reverse biased diode having characteristics identical to those of the first diode.

15. Device according claims 1, wherein the first impedance adapters have respective gains which are substantially equal.

16. Device according to claim 1, wherein the working electrodes include at least one reference electrode.

17. Device according to claim 1, wherein there are at least three acquisition electrodes, and the processor is capable of calculating a notional reference potential from signals delivered by each acquisition electrode.

18. Device according to claim 1, wherein the supply includes at least one of a battery and rechargeable accumulators, the potential difference at terminals thereof being substantially equal to 9 volts.

19. Device according to claim 1, wherein the supply includes a DC—DC converter.

20. Device according to claim 1, wherein the sensor equipment is an electrophysiological helmet that can be fitted on the cranium of the subject, and the signals detected by the at least one acquisition electrode are cerebral activity waves issuing from identifiable areas of the brain.

21. Electrophysiological device, comprising:
   sensor equipment that can be fitted to a subject, and provided with a set of electrodes for detecting electromagnetic signals, in order to deliver output signals to inputs of a processing means capable of processing the signals prior to storage, the set of electrodes including working electrodes having at least one acquisition electrode to be connected to the processing means as a floating ground,
   wherein an output of each working electrode is equipped with first impedance adapter means;
   a common electrical supply for the first impedance adapter means; and
   a circuit, capable of maintaining an intermediate electrical potential, dependant from the supply, at an electrical potential of the additional electrode,
   wherein the output of the additional electrode is equipped with second impedance adapter means also fed by the supply,
   wherein each of the first and second impedance adapter means is an operational amplifier including inverting inputs, non-inverting inputs, and an output, and
   wherein the circuit of the additional electrode includes a first resistor, between a first end terminal of the supply and the non-inverting input of the second impedance adapter operation amplifier, and also a second resistor, equal in value to the first resistor, between a second end terminal of the supply and the non-inverting input of the second impedance adapter operational amplifier.

22. Device according to claim 21, wherein the operational amplifier with which the additional electrode is equipped is a bipolar type.

23. Device according to claim 21, wherein the operational amplifier with which the additional electrode is equipped is a field effect type.

24. Device according to claim 21, wherein each operational amplifier, with which a working electrode is equipped, is a bipolar type.

25. Device according to claim 21, wherein each operational amplifier, with which a working electrode is equipped, is a field effect type.

26. Device according to claim 25, further comprising, between the first end terminal of the supply and the non-inverting input of each operational amplifier corresponding to each working electrode, a first, reverse biased diode and, between the second end terminal of said supply and the non-inverting input of each operational amplifier corresponding to each working electrode, a second reverse biased diode having characteristics identical to those of the first diode.

27. Device according to claim 21, wherein the working electrodes include at least one reference electrode.

28. Device according to claim 21, wherein there are at least three acquisition electrodes, and the processor is capable of calculating a notional reference potential from signals delivered by each acquisition electrode.

29. Device according to claim 21, wherein the supply includes at least one of a battery and rechargeable accumulators, the potential difference at terminals thereof being substantially equal to 9 volts.

30. Device according to claim 21, wherein the supply includes a DC—DC converter.

31. Device according to claim 21, wherein the sensor equipment is an electrophysiological helmet that can be fitted on the cranium of the subject, and the signals detected by the at least one acquisition electrode are cerebral activity waves issuing from identifiable areas of the brain.

32. Electrophysiological device, comprising:
   sensor equipment that can be fitted to a subject, and provided with a set of electrodes for detecting electromagnetic signals, in order to deliver output signals to inputs of a processing means capable of processing the signals prior to storage, the set of electrodes including working electrodes having at least one acquisition electrode to be connected to the processing means as a floating ground,
   wherein an output of each working electrode is equipped with first impedance adapter means;
   a common electrical supply for the first impedance adapter means; and
   a circuit, capable of maintaining an intermediate electrical potential, dependant from the supply at an electrical potential of the additional electrode;
   wherein the output of the additional electrode is equipped with second impedance adapter means also fed by the supply,
   wherein each of the first and second impedance adapter means is an operational amplifier including inverting inputs, non-inverting inputs, and an output, and
   wherein each operational amplifier with which a working electrode is equipped is of a field effect type;
   between a first end terminal of the supply and the non-inverting input of each operational amplifier corresponding to each working electrode, a first, reverse biased diode; and between a second end terminal of said supply and the non-inverting input of each operational amplifier corresponding to each working electrode, a second, reverse biased diode, having characteristics identical to those of the first diodes.

33. Device according to claim 32, wherein the working electrodes include at least one reference electrode.

34. Device according to claim 32, wherein there are at least three acquisition electrodes, and the processor is capable of calculating a notional reference potential from signals delivered by each acquisition electrode.

35. Device according to claim 32, wherein the supply includes at least one of a battery and rechargeable accumulators, the potential difference at terminals thereof being substantially equal to 9 volts.

36. Device according to claim 32, wherein the supply includes a DC—DC converter.

37. Device according to claim 32, wherein the sensor equipment is an electrophysiological helmet that can be fitted on the cranium of the subject, and the signals detected by the at least one acquisition electrode are cerebral activity waves issuing from identifiable areas of the brain.

* * * * *